United States Patent [19]

Hupf

[11] Patent Number: 5,531,095
[45] Date of Patent: Jul. 2, 1996

[54] METHOD AND APPARATUS FOR DETERMINING THE MECHANICAL DURABILITY OF THE SURFACE FINISH OF A COOKING VESSEL

[75] Inventor: Charles J. Hupf, Cascade, Wis.

[73] Assignee: Regal Ware, Inc., Kewaskum, Wis.

[21] Appl. No.: 182,921

[22] Filed: Jan. 14, 1994

[51] Int. Cl.$^6$ ................................................. G01N 3/56
[52] U.S. Cl. ................................................................. 73/7
[58] Field of Search ....................................................... 73/7

[56] References Cited

U.S. PATENT DOCUMENTS

| | | | |
|---|---|---|---|
| 1,444,803 | 2/1923 | Ratner et al. | 73/7 |
| 2,032,202 | 2/1936 | Dennis | 73/7 |
| 2,114,029 | 4/1938 | Perry | 73/7 |
| 2,962,890 | 12/1990 | Burrino | 73/7 |
| 3,664,888 | 5/1972 | Oga et al. | 148/272 |
| 4,285,728 | 8/1981 | Babcock et al. | 501/7 |
| 4,751,016 | 6/1988 | Tse et al. | 252/174.25 |
| 4,914,146 | 4/1990 | Honda et al. | 524/449 |
| 4,936,135 | 6/1990 | Annis et al. | 73/7 |
| 5,106,682 | 4/1992 | Matsushita et al. | 428/324 |
| 5,326,728 | 7/1994 | Boury et al. | 501/17 |

FOREIGN PATENT DOCUMENTS

| | | | |
|---|---|---|---|
| 226631 | 10/1986 | Japan | 73/7 |
| 173475 | 9/1965 | U.S.S.R. | 73/7 |
| 195182 | 6/1967 | U.S.S.R. | 73/7 |

*Primary Examiner*—Thomas P. Noland
*Attorney, Agent, or Firm*—Wheeler & Kromholz

[57] ABSTRACT

The apparatus comprised of a web of material having an abrasive surface, a rotary moving mechanism for rotatably moving the web of material around a predetermined point of the web of material, and a connecting mechanism for connecting the predetermined point of the web of material to the rotary moving mechanism. The apparatus including a cyclic moving mechanism for moving either the abrasive surface of the web of material in a cyclic pattern over and against the surface finish of the cooking vessel for a predetermined period of time or for moving the cooking vessel so that the surface finish of the cooking vessel moves in a cyclic pattern against the abrasive surface of the web of material for a predetermined period of time. The method is generally performed as follows: Adjusting the rotary moving mechanism so that it applies a predetermined pressure or force to the surface finish and so that it rotatably moves the web of material in at least one predetermined direction at a predetermined rate of speed; the direction could be one way or reversible. Bringing the abrasive surface of the material into contact with the surface finish of the cooking vessel. Actuating the rotary moving mechanism so that the abrasive surface is moved at a predetermined speed for a predetermined time while the cyclic moving mechanism moves the cooking vessel in a predetermined pattern for the predetermined time. Measuring the final thickness of the surface finish of the cooking vessel at the predetermined area of the surface finish and determining the difference between the thickness determined in step one and the final thickness of the surface finish.

8 Claims, 3 Drawing Sheets

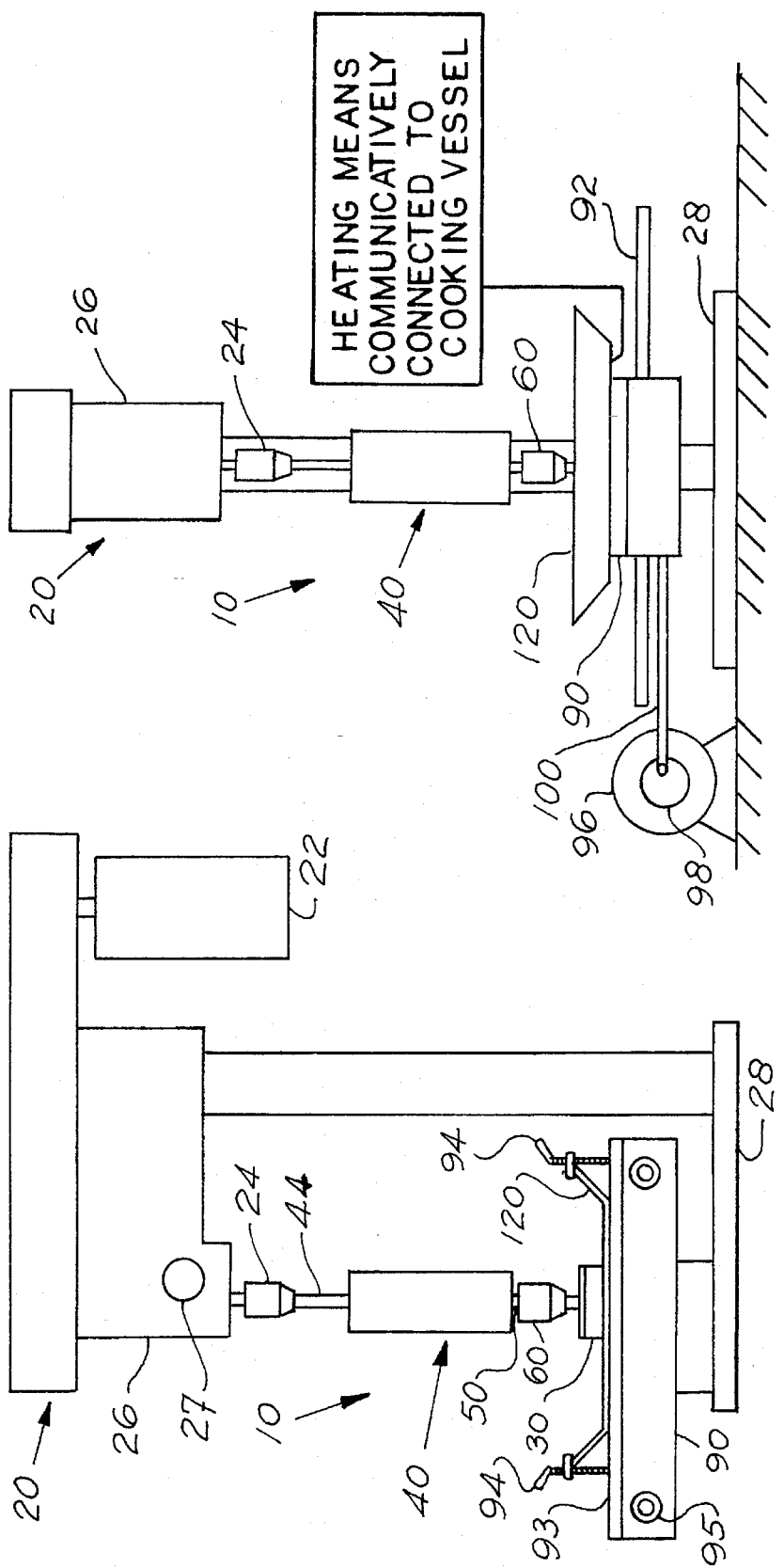

METHOD AND APPARATUS FOR DETERMINING THE MECHANICAL DURABILITY OF THE SURFACE FINISH OF A COOKING VESSEL

BACKGROUND OF THE INVENTION

The present invention relates generally to the field of durability testing and specifically to a unique test designed to determine the durability of the surface finish of a cooking vessel.

The surface finish of a cooking vessel may be made of many different types of materials. Currently, it is very desirable to have a nonstick surface coating applied to the cooking surface of a cooking vessel. This type of surface coating is desired because it makes the cooking vessel generally easier to clean and use.

One problem with these types of surfaces is that they tend to be softer than other types of surfaces for cooking vessels. Tending to be softer, they are much more susceptible to scuffing that eventually causes the surface to wear or tear away revealing the bare material, usually metal, to which the nonstick coating was applied. Consequently, it is desirable to have a testing procedure that can accurately and precisely inform the manufacturer of the durability of his or her coating so that the public may be accurately informed about the amount of scuffing or other abrasion that the cooking surface can safely sustain. Further, such a testing method allows the manufacturer to accurately gauge the quality of the surfaces produced in a definitive manner by providing the manufacturer with a process and an apparatus that allows for consistent testing of the surface of the cooking vessel.

Accordingly, it is the chief of objective of the present invention to provide a testing method and an apparatus that allows accurate testing of the durability of a nonstick surface of a cooking vessel.

It is a further objective of the present invention to provide a testing method and an apparatus that allows accurate testing of the durability of any type of surface of a cooking vessel; e.g. an anodized surface, a thermally applied surface like an arc spray or flame spray surface, or any other type of material that may be the surface of a cooking vessel.

DEFINITION OF TERMS

For the purposes of clarity the terms given below shall be interpreted throughout the specification and the claims as having the following definitions.

"Surface finish" means the surface of a cooking vessel or the combination of a surface coating with any other material that is used as a substrate layer for the application of a surface coating like a nonstick coating.

"Moved relative to each other" encompasses all manner of movement that the objects referred to by the phrase may be moved. For example, as discussed below, the surface finish may be stationary and the abrasive material may be moved, the abrasive material may be stationary and the surface finish (by moving the cooking vessel) may be moved, or both the surface finish and the abrasive material may be moved simultaneously.

SUMMARY OF THE INVENTION

The invention is a method of testing and an apparatus for carrying out the test procedure.

The apparatus for determining the mechanical durability of a surface finish of a cooking vessel is comprised of a web of material having an abrasive surface (the material that composes the abrasive surface may be uniformly or randomly distributed across the abrasive surface), a rotary moving mechanism for rotatably moving the web of material around a predetermined point of the web of material, and a connecting mechanism for connecting the predetermined point of the web of material to the rotary moving mechanism.

The apparatus further includes a cyclic moving mechanism for moving either the abrasive surface of the web of material in a cyclic pattern over and against the surface finish of the cooking vessel for a predetermined period of time or for moving the cooking vessel so that the surface finish of the cooking vessel moves in a cyclic pattern against the abrasive surface of the web of material for a predetermined period of time.

The method for determining the mechanical durability of the surface finish of a cooking vessel uses the aforesaid apparatus. The method is generally performed as follows: Adjusting the rotary moving mechanism so that it applies a predetermined pressure or force to the surface finish and so that it rotatably moves the web of material in at least one predetermined direction at a predetermined rate of speed; the direction could be one way or reversible. Bringing the abrasive surface of the material into contact with the surface finish of the cooking vessel. Actuating the rotary moving mechanism so that the abrasive surface is moved at a predetermined speed for a predetermined time while the cyclic moving mechanism moves the cooking vessel in a predetermined pattern for the predetermined time. Measuring the final thickness of the surface finish of the cooking vessel at the predetermined area of the surface finish and determining the difference between the initial thickness determined in step one and the final thickness of the surface finish.

Alternatively, the method could be simply accomplished by abrading the surface finish of the cooking vessel by applying a rotary driven material at a predetermined force or pressure to the surface finish for a predetermined time and at a predetermined speed. If more rigorous testing were required the method could be expanded to further include moving the surface finish and the material in a predetermined pattern relative to one another. Additionally, the testing method could be made still more rigorous by repeating the predetermined pattern in which the surface finish and material are moved relative to each other so that the predetermined pattern is repeated in a cyclic manner.

These and other benefits of the present invention will be apparent to one skilled in the art from the following description.

DESCRIPTION OF THE DRAWINGS

FIG. 1 is a partially cut away side view of my apparatus for determining the mechanical durability of the surface finish of a cooking vessel.

FIG. 2 is a front view of my apparatus for determining the mechanical durability of the surface finish of a cooking vessel.

DETAILED DESCRIPTION

Figure 3:
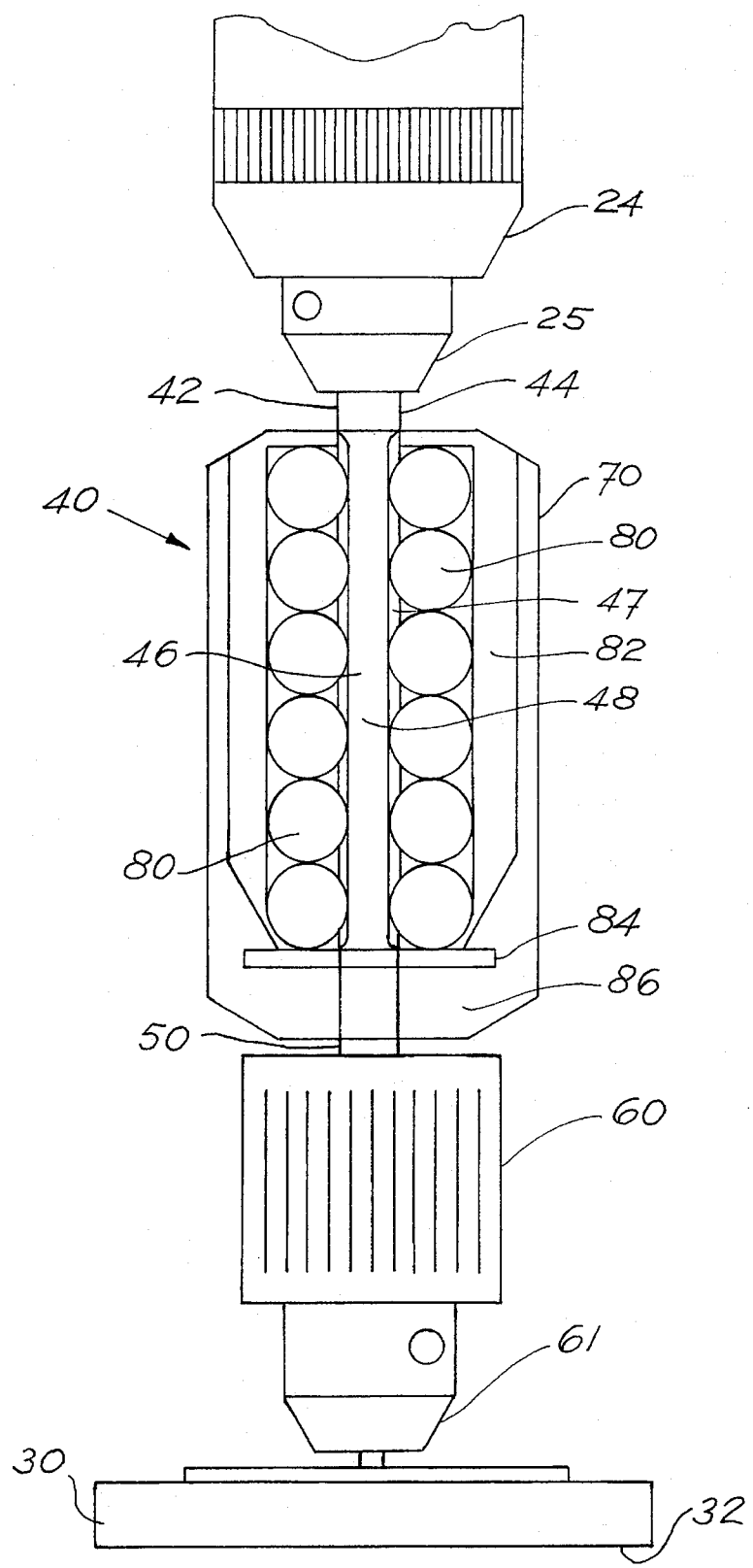
FIG. 3 is a partially cut away front view of the force transferring mechanism of my apparatus for determining the mechanical durability of the surface finish of a cooking vessel.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

With reference to the drawings in general, and to FIGS. 1 and 2 in particular, the apparatus for determining the mechanical durability of the surface finish of a cooking vessel is generally shown as 10.

The apparatus 10 comprises a drill press 20, a force transferring mechanism 40, a web of abrasive material 30, and a linear table 90. As shown in FIGS. 1 and 2, the drill press 20 is powered by motor 22. The motor 22 turns first chuck 24 at a rate of speed that is determined by the gearing selected within drill press gear box 26. In the present embodiment of the invention that speed is 200 rpm. The drill press 20 further includes a device 27 for raising and lowering the position of first chuck 24.

Attached to the clamping means 25 of the first chuck 24 is the input end 44 of drive rod 42 of force transferring mechanism 40. In the present embodiment, a Saginaw bearing manufactured by the Saginaw Manufacturing Company of Saginaw, Mich. is used. Drive rod 42 is precision ground. Input end 44 of drive rod 42 has a generally round cross-section. The middle portion 46 of drive rod 42 is fluted and has (3) three flutes 48 in the present embodiment as shown in FIG. 3. These flutes 48 help hold bearings 50 is place and provide surface against which force transmitted through the bearings 80 is applied when the drive rod 42 is turned. The output end 50 of drive rod 42 is attached to a second chuck 60. Also, similar to the input end 44, output end 50 has a generally round cross section.

The force transferring mechanism 40 further includes a housing 70. Within housing 70 and surrounding fluted portions 46 of shaft 42 is located a series of bearings 80. Each bearing 80 fits into a longitudinal or axial recession 47 of the flutes 48. Each bearing 80 is further supported by outer race 82. A washer 84 is located at the bottom of race 82 so that bearings 80 do not fall out of their position. A free or floating space 86 is located just beneath washer 84. The function of the force transferring mechanism 40 is to eliminate the vertical moment when the abrasive surface 32 of the material 30 is frictionally engaged with the surface finish 126 of the cooking vessel 120 when the method of the present invention is performed. Thus only a constant vertical or downward force or pressure is exerted upon the abrasive surface 32 regardless of the level of lateral or horizontal motion or force applied to the force transferring mechanism 40.

Attached to the clamping means 61 of second chuck 60 is the web of material 30. The web 30 is generally a round, disc-like structure. It is composed of material which has randomly distributed over its surface abrasive material.

Also, the web 30 may be made out of any suitable material. In the present invention, the web 30 is a Scotch brand abrasive disk (sold by 3M; Minnesota Mining and Manufacturing Corporation of Minnesota) but it could also be a steel wool pad or any other type of abrasive. Depending on the rigorousness desired the grade of abrasive disk or pad used may be varied. In the present invention the method of test may run three times using three different level of abrasive disks; e.g. very fine grade, medium grade, and coarse grade.

Linear table 90, as shown in FIGS. 1 and 2, is positioned just above the base 28 of drill press 20. The linear table includes a top surface 93 to which a pair of clamps 94 are attached. The clamps 94 hold the cooking vessel 120 to be tested in the desired position. Linear table 90 moves laterally in one direction on shafts 92. Shafts 92 fit into bearings 95 that are pressed into the linear table 90.

A second motor 96 has an offset cam 98 attached to its output shaft. The offset cam 98 is connected to the linear table 90 by connecting rod 100. When motor 96 is energized, offset cam 98 rotates and cycles linear table 90 back and forth on shafts 92 at a rate of 34 lateral cycles per minute. Please note that table 90 could also be designed to move along two (2) or even three (3) axes of movement to produce patterns of wear that are nonlinear; e.g. triangular shapes or patterns, square shapes or patterns, circular shapes or patterns, etc.

Figure 4:
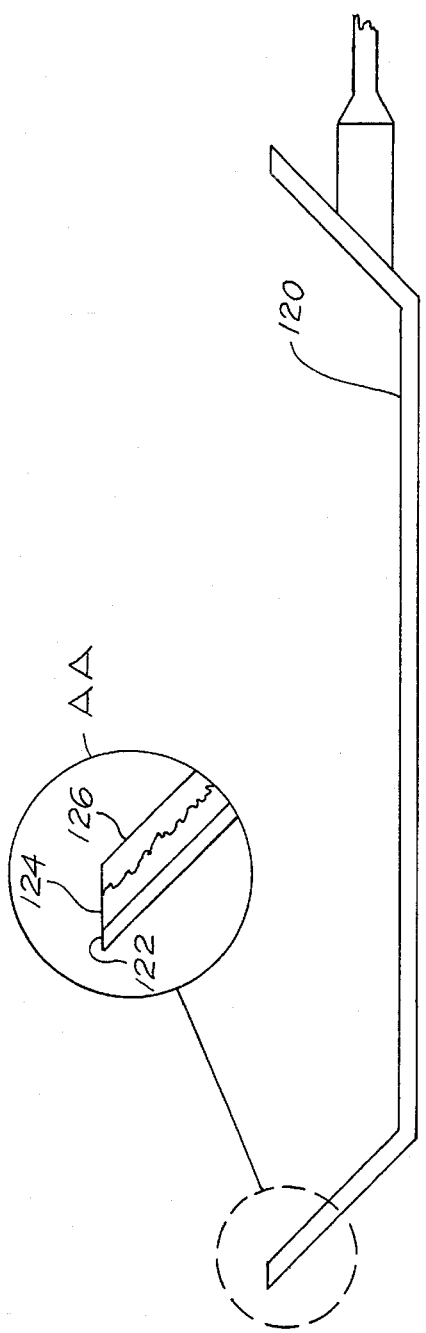
FIG. 4 is a sectional view of cooking vessel including an exploded view to show the different layers of material used in the cooking vessel construction.

As shown in FIG. 4, a typical cooking vessel 120 has a plurality of layers. The first layer 122 is typically the base metal. Most commonly, this material is aluminum or stainless steel. Next, layer 124 is a thermally sprayed (arc or flame sprayed) layer that is applied to base metal layer 122. Thermally sprayed material 124 usually produces a very rough surface finish as shown in the exploded portion AA of FIG. 4. Finally, a non-stick coating 126, such as TEFLON®, is applied to thermally sprayed material 124. Typically, the thermally sprayed material 124 is either stainless steel or aluminum but could be any other suitable material. Further, the thermally sprayed material is considered to be part of the surface finish 126 in the present invention.

Figure 5:
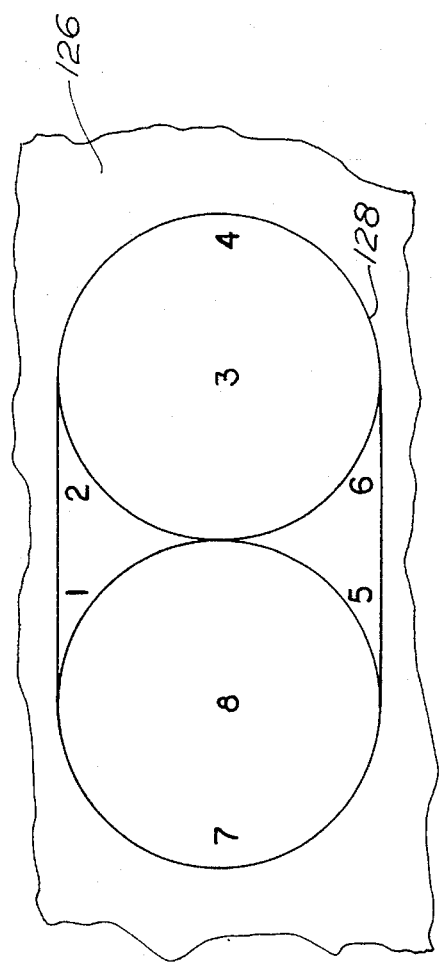
FIG. 5 is a top plan view of a section of the cooking vessel showing the surface finish and the predetermined area to be tested and the points at which the thickness of the surface finish are preferably measured prior to and after testing by the method of the present invention.

The cooking vessel 120 is tested in my apparatus 10 as follows: First, the thickness of the surface finish 126 of the cooking vessel 120 is determined using a Fischerscope Magna, Eddy, Multi 750 of the type sold by Fischer Technology, Inc. of 750 Marshall Phelps Road, Windsor, Conn. 06095-2199; This is preferred although any other method may also be used, e.g. a micrometer. The measurements are recommended to be taken at eight (8) points (See FIG. 5—points 1–8) over the predetermined area 128 of the surface finish 126 that is to be tested. See FIG. 5. Fewer or more measurements could be taken or selected depending upon the level of accuracy desired and the precision of the measuring tool used.

The cooking vessel 120 is then positioned on the linear table 90 so that the abrasive surface 32 of the web of material 30 will contact the predetermined area 128 of the surface finish 126. Next, the cooking vessel 120 is clamped to the linear table 90 using clamps 94. The drill press 20 is then adjusted to apply a predetermined amount of force, preferably about 1.256 pounds or 0.57 Kg when using a two (2) inch diameter web 30, to the surface finish 126. Linear table 90 is adjusted to travel back and forth two (2) inches per cycle at a rate of 34 cycles per minute. The travel distance being substantially equal to the diameter or width of the web of material 30; the web 30, as previously noted, preferably being disc shaped. At the same time the drill press 20 is actuated and web 30 begins to rotate so that abrasive surface 32 begins abrading the surface finish 126 and linear table 90 is energized to move the cooking vessel 120 in a predetermined pattern for a specified period of time, typically one (1) hour. When the testing time period has elapsed, the thickness of cooking vessel 120 is again measured using the Fischerscope Magna, Eddy, Multi 750 at the same eight (8) points where it was originally measured. Finally, the difference between surface finish 126 of the cooking vessel 120's initial thickness and the final thickness of the surface finish 126 is computed. The difference is then used to determine the mechanical durability of the surface finish 126 of the cooking vessel 120.

Alternatively, the method of the present invention may also include an additional procedure in which the cooking vessel 120 is heated while being abraded. For example, the cooking vessel 120 could be heated to cooking temperatures so that the effect of abrasion or the resistance to abrasion at cooking temperatures could be evaluated.

The foregoing is considered as illustrative only of the principles of the invention. Furthermore, since numerous modifications and changes will readily occur to those skilled in the art, it is not desired to limit the invention to the exact construction and operation shown and described.

What is claimed is:

1. An apparatus for determining the mechanical durability of a surface finish of a cooking vessel, the apparatus comprising:

a web of material having an abrasive surface;

a stationary base;

a rotary motor connected to the base, the rotary motor having a first connector;

a force transferring mechanism having an input and an output, the input connected to the first connector;

a predetermined point of the web of material connected to the output;

a linear table connected to the base, the linear table having at least one clamp for clamping the cooking vessel to the table;

a reciprocating motor connected to the linear table.

2. The apparatus of claim 1 wherein the reciprocating motor is connected to the linear table and the base remains stationary.

3. The apparatus of claim 1 wherein the rotary motor comprises a drill press.

4. The apparatus of claim 1 further including a heating heating means communicatively connected to the cooking vessel.

5. The apparatus of claim 1 wherein the web comprises a steelwool pad.

6. A method for determining the mechanical durability of the surface finish of a cooking vessel using an apparatus having a web of material having an abrasive surface and a predetermined point, a stationary base, a rotary motor connected to the base, the rotary motor having a first connector, a force transferring mechanism having an input and an output, the input connected to the first connector, a predetermined point of the web of material connected to the output, a linear table connected to the base, the linear table having at least one clamp for damping the cooking vessel to the table, a reciprocating motor connected to the linear table, the method comprising:

clamping the cooking vessel to the linear table;

measuring the initial thickness of the surface finish of the cooking vessel;

actuating the rotary motor;

bringing the web into contact with the surface finish of the cooking vessel and applying a predetermined force;

actuating the reciprocating motor for a predetermined period of time;

measuring the final thickness of the surface finish of the cooking vessel.

7. The method of claim 6 further including a step of heating the cooking vessel.

8. The method of claim 6 wherein the initial and final thickness measurements are taken at a plurality of points.

* * * * *